United States Patent [19]

Baroni et al.

[11] Patent Number: 5,723,611

[45] Date of Patent: Mar. 3, 1998

[54] HETEROARYLPIPERIDINES

[75] Inventors: Marco Baroni, Vanzago; Tiziano Croci, Milan; Marco Landi, Bussero; Umberto Guzzi, Milan, all of Italy; Dino Nisato, Saint Georges D'Orques, France

[73] Assignee: Sanofi, Paris, France

[21] Appl. No.: 469,523

[22] Filed: Jun. 6, 1995

Related U.S. Application Data

[62] Division of Ser. No. 319,595, Oct. 7, 1994, Pat. No. 5,502,063.

[30] Foreign Application Priority Data

Oct. 11, 1993 [EP] European Pat. Off. ............ 93402498

[51] Int. Cl.$^6$ .................... C07D 239/42; C07D 401/04
[52] U.S. Cl. .................... 544/330; 544/334; 544/336; 544/409; 546/193; 546/233; 546/244
[58] Field of Search ............... 514/255, 256, 514/275, 315, 318; 544/334, 336, 330, 409; 546/193, 233, 244

[56] References Cited

U.S. PATENT DOCUMENTS 5,196,439  3/1993  Sugimoto et al. ............... 546/244
5,447,931  9/1995  Baroni et al. ................... 514/252
5,502,063  3/1996  Baroni et al. ................... 514/318

Primary Examiner—Yogendra N. Gupta
Attorney, Agent, or Firm—Bacon & Thomas

[57] ABSTRACT

A compound of formula (VIII):

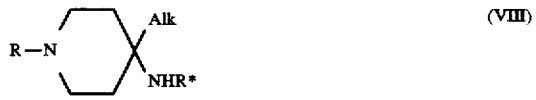

in which Alk is a $(C_1-C_4)$alkyl group, R* is hydrogen or a protecting group cleavable by hydrolysis and R is hydrogen, a protecting group cleavable by reduction or a heterocycle of structure (IX):

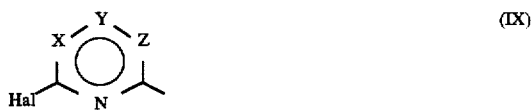

in which Hal is a halogen atom and X, Y and Z are each —CH= or one of them is a nitrogen atom and the others are —CH=, and its salts, R* being other than hydrogen if R is hydrogen or a group of structure (IX).

2 Claims, No Drawings

HETEROARYLPIPERIDINES

This application is a Division of application Ser. No. 08/319,595, filed Oct. 7, 1994, U.S. Pat No. 5,502,063.

The present invention relates to novel 1-heteroaryl-4-alkyl-4-aminopiperidines active as sero toninergic 5-HT$_3$ agonists, to the process for their preparation and to the pharmaceutical compositions in which they are present.

Certain 4-amino-1-(pyridin-2-yl)piperidines are described in patent EP-B-21973 as anorexigenic agents. The activity of these compounds as serotoninergic 5-HT$_3$ agonists is illustrated in patent application EP-A-506 545.

It has now been found that the introduction of an alkyl group into the 4-position of these 4-amino-1-(pyridin-2-yl) piperidines gives 5-HT$_3$ agonists which are more potent and more selective then the known products, and it has also been found that the derivatives with a pyrimidine or pyrazine ring in place of the pyridine have the same activity and a very good selectivity.

Thus, according to one of its features, the present invention relates to novel 1-heteroaryl-4-alkyl-4-aminopiperidines of formula (I):

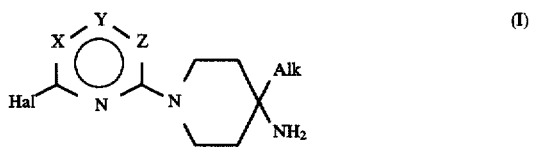

in which Hal is a halogen atom, Alk is a (C$_1$–C$_4$)alkyl group and X, Y and Z are each —C= or one of them is a nitrogen atom and the other two are —CH=, and their pharmaceutically acceptable or unacceptable salts.

In the present description, the terms "halogen atom" and "halogeno" preferably denote chlorine and bromine but can also be a fluorine or iodine atom; the term "(C$_1$–C$_4$)alkyl" denotes a linear or branched alkyl radical containing 1 to 4 carbon atoms, such as the methyl and ethyl radicals.

The compounds of formula (I) in which Hal is a chlorine atom and Alk is a methyl group, and their salts, are particularly advantageous compounds.

Among these compounds, 4-amino-1-(6-chloropyridin-2-yl)-4-methylpiperidine and its pharmaceutically acceptable salts, especially its hydrochloride, 4-amino-1-(4-chloropyrimidin-2-yl)-4-methylpiperidine and its pharmaceutically acceptable salts, especially its maleate, 4-amino-1-(2-chloropyrimidin-4-yl)-4-methylpiperidine and its pharmaceutically acceptable salts, especially its maleate, and 4-amino-1-(6-chloropyrazin-2-yl)-4-methylpiperidine and its pharmaceutically acceptable salts, especially its hydrochloride and its maleate, are particularly preferred.

According to another of its features, the present invention relates to a process for the preparation of the 1-heteroaryl-4-alkyl-4-aminopiperidines of formula (I) above, which comprises:

(a) treating an NH-protected 4-alkyl-1,2,3,6-tetrahydropyridine of formula (II):

in which Alk is an alkyl group having 1 to 4 carbon atoms and P' is an NH-protecting group cleavable by reduction, with acetonitrile and sulfuric acid and isolating an NH-protected 4-acetylamino-4-alkylpiperidine of formula (III'):

in which P' and Alk are as defined above, and then, if appropriate, (a') subjecting the resulting compound (III') to NH$_2$-deprotection by hydrolysis to give an NH-protected 4-alkyl-4-aminopiperidine of formula (IV):

in which P' and Alk are as defined above, and (a") protecting the primary amino group with a group, other than the acetyl group, cleavable by hydrolysis;

(b) subjecting the resulting diprotected 4-alkyl-4-aminopiperidine of formula (III):

in which P' and Alk are as defined above and P* is an NH$_2$-protecting group cleavable by hydrolysis, to NH-deprotection by reduction;

(c) treating the resulting NH$_2$-protected 4-alkyl-4-aminopiperdine of formula (V):

in which P* and Alk are as defined above, with a dihalogenoheteroaryl compound of formula (VI):

in which Hal, X, Y and Z are as defined above;

(d) hydrolyzing the resulting compound of formula (VII):

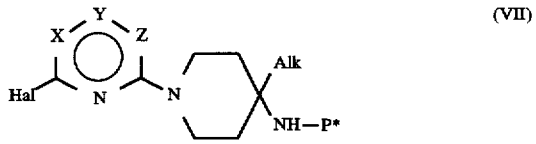

in which Hal is a halogen and X, Y, Z, Alk and P* are as defined above; and (e) isolating the resulting product (I) as such or in the form of one of its salts, or converting it to one of its salts.

The terms "NH-protection", "NH-deprotection", "NH-protected" and "NH-deprotected", as used in the present description and in the claims and relating to the "NH-deprotecting" group P', refer to the protection and deprotection of the secondary amine, namely the nitrogen occupying the 1-position of the piperidine. Analogously, the terms "NH$_2$-protection", "NH$_2$-deprotection", "NH$_2$-protected" and "NH$_2$-deprotected", relating to the "NH$_2$-protecting" group P*, refer to the protection and deprotection of the primary amine, namely the amine in the 4-position of the piperidine.

In the present description, the term "protecting group" denotes an amino-protecting group of the type employed in peptide synthesis, examples being acyl groups such as formyl, acetyl, propionyl, phenylacetyl, phenoxyacetyl and the like; an alkoxycarbonyl group such as t-butoxycarbonyl (BOC) and the like; an alkoxyalkylcarbonyl group such as methoxypropionyl and the like; a substituted alkoxycarbonyl group such as trichloroethoxycarbonyl and the like; a substituted alkylcarbonyl group such as monochloromethylcarbonyl, monochloroethylcarbonyl, dichloromethylcarbonyl, trichloromethylcarbonyl, trichloroethylcarbonyl, trichloropropylcarbonyl, trifluoromethylcarbonyl and the like; an arylalkoxycarbonyl group such as benzyloxycarbonyl and the like; a substituted arylalkoxycarbonyl group such as 4-nitrobenzyloxycarbonyl and the like; a benzyl group; a substituted benzyl group; an optionally substituted diphenylmethyl group; an optionally substituted trityl group such as 4-methoxyphenyldiphenylmethyl or di(4-methoxyphenyl) phenylmethyl; and a silylating group such as trimethylsilyl, ethyldimethylsilyl or t-butyldimethylsilyl and the like.

Said protecting groups can be cleaved by the conventional methods, for example by reduction or hydrolysis. A more detailed description of these amino-protecting groups, together with methods for their preparation and their elimination, is given for example by T. W. Greene, "Protective Groups in Organic Synthesis", John Wiley & Sons, 1981, and by J. F. W. McOmie, "Protective Groups in Organic Chemistry", Plenum Press, 1973.

In the present description, the NH-protecting group represented by P' is by definition a group clearable by reduction, and the $NH_2$-protecting group represented by P* is by definition a group clearable hydrolysis.

A preferred NH-protecting group P' is the benzyl group optionally substituted on the aromatic ring, for example by a methoxy or nitro group or by a chlorine atom, preferably in the 4-position, the unsubstituted benzyl group being particularly preferred. This group is eliminated by catalytic hydrogenation, preferably using palladium-on-charcoal as the catalyst.

Preferred $NH_2$-protecting groups P* are $C_1$–$C_4$-alkanoyl, trifluoroacetyl and $C_1$–$C_4$-alkoxycarbonyl groups, acetyl and t-butoxycarbonyl (BOC) groups being particularly preferred. These groups are eliminated by hydrolysis in an acid medium, for example with hydrochloric or trifluoroacetic acid.

The starting 1,2,3,6-tetrahydropyridines of formula (II) in which P' is a benzyl or substituted benzyl group are products known in the literature. They can be prepared by the methods described in patent DE 2101997, in J. Am. Chem. Soc., 1985, 107, 1768–1769, and in Organic Synthesis, 70, 111–119, 1992. The compounds of formula (II) in which P' is a protecting group clearable by reduction, other than the benzyl group, can be prepared by the same method.

Step (a), which is a Ritter reaction, is performed by using an approximately twofold excess of acetonitrile relative to the starting compound (II) and by adding excess concentrated sulfuric acid to the compound (II)/acetonitrile mixture. After heating at between 50° C. and the reflux temperature, preferably at 60°–80° C., for 18–30 hours, the compound of formula (III) is isolated by neutralization of the excess acid, extraction with a solvent such as ether or tetrahydrofuran, evaporation of the solvent and taking-up or crystallization of the residue.

The resulting compound (III') can be subjected to step (b) directly. For reasons of reactivity, however, it may be appropriate to convert the acetyl group to another protecting group also clearable by hydrolysis. Thus, in the optional additional step (a'), the compound (III) is subjected to hydrolysis, advantageously in an acid medium, and converted to the NH-protected 4-alkyl-4-aminopiperidine of formula (IV).

This $NH_2$-deprotection by cleavage of the acetyl group is effected by heating for 24–48 hours with a strong acid such as hydrochloric acid. The product of formula (IV) is isolated by neutralization of the reaction mixture and purification of the residue by crystallization or chromatography.

Then, in the second optional additional step (a"), the compound (IV) is subjected to $NH_2$-protection by the conventional methods, which are illustrated for example in the two works cited above, so as to protect the primary amine with a protecting group clearable by hydrolysis, other than the acetyl group.

This $NH_2$-protection is effected using the appropriate known reagents based on the chosen $NH_2$-protecting group other than acetyl. Thus, if the chosen group is an acyl group such as t-butoxycarbonyl or trifluoroacetyl, the compound (IV) is treated with a functional derivative of said acid, for example the chloride, the anhydride, a mixed anhydride, an ester or an activated ester, for example the 4-nitrobenzyl ester. If the chosen $NH_2$-protecting group is a non-acylating group, for example a trityl or trimethylsilyl group, the compound (IV) is treated with a halide of the chosen group, for example triphenylchloromethane or trimethylchlorosilane, or with another well-known reactive compound such as bis-trimethylsilylacetamide.

In step (b) of the process of the present invention, the deprotected 4-amino-4-alkylpiperidine of formula (III) obtained at the end of step (a), or, if appropriate, at the end of the additional steps (a') and (a"), is subjected to selective NH-deprotection by elimination of the group P'. Said NH-deprotection is effected by reduction, especially by hydrogenation in the presence of an appropriate catalyst, 5–15% palladium-on-charcoal, preferably 10% palladium-on-charcoal, generally being usable as the catalyst. The hydrogenation is carried out in a polar or apolar, protic or aprotic organic solvent, for example in an alkenol such as ethanol. The NH-deprotected compound of formula (V) is isolated by the conventional techniques, for example by filtration of the catalyst and its support, evaporation of the solvent and taking-up of the residue with an appropriate solvent such as ethyl acetate or an ether.

In step (c), the condensation reaction giving the compound of formula (VII) is appropriately carried out in an organic solvent such as an alcohol, dimethylformamide, dimethyl sulfoxide, sulfolane, acetonitrile, pyridine and the like, at a temperature generally between 50° C. and the reflux tamporature of the chosen solvent, in the presence of a basic condensation agent such as an alkali metal hydroxide, carbonate or bicarbonate or a tertiary amine.

The compound of formula (VII) is isolated by the usual techniques, for example by evaporation of the solvent, optional purification by taking-up of the residue with an appropriate solvent and chromatography or crystallization.

In step (d), the $NH_2$-deprotection is effected by eliminating the group P*, which is hydrolyzed, especially in an acid medium. The conditions are exactly the same as those illustrated above for step (a") if the group P* is an acetyl group (formula III'). For other protecting groups, the appropriate techniques which are well known for this type of cleavage are used. For example, the preferred $NH_2$-protecting group, t-butoxycarbonyl, is cleaved by reaction with trifluoroacetic acid.

The resulting product of formula (I) is isolated by the known methods. If the $NH_2$-deprotection of step (d) of the process of the present invention is effected by hydrolysis in an acid medium, the product of formula (I) can be isolated as an addition salt with the acid used. The reaction mixture obtained after hydrolysis can also be neutralized with a base such as sodium or potassium hydroxide or ammonium hydroxide, so as to isolate the free base of formula (I). The latter can in turn be converted to an addition salt with an acid other than that used for hydrolysis. This operation is desirable if the hydrolysis is carried out with a pharmaceutically unacceptable acid such as trifluoroacetic acid.

The salts of the compounds of formula (I) are easily prepared in a manner known per se by reacting the chosen acid with the compound of formula (I) dissolved for example in acetone, ether or an alcohol such as methanol, ethanol or isopropanol.

When the salts of the compounds of formula (I) are prepared for administration as drugs, the acids employed must be pharmaceutically acceptable acids; if salts of the compounds of formula (I) are prepared for another purpose, for example for improving the purification of the product or performing analytical tests more satisfactorily, any addition acid can then be used.

The pharmaceutically acceptable salts of the compounds of formula (I) include the addition salts with physiologically compatible mineral or organic acids, for example the salts formed with hydrochloric, hydrobromic, hydriodic, nitric, sulfuric, phosphoric, propionic, acetic, formic, benzoic, maleic, fumaric, succinic, tartaric, citric, aspartic and ascorbic acids and sulfonic acids such as methanesulfonic, ethanesulfonic, 2-hydroxyethanesulfonic, naphthalane-2-sulfonic, benzenesulfonic or p-toluenesulfonic acid.

The compounds of formulae (III), (IV), (V) and (VII) required for the synthesis of the compounds of formula (I), the preparation of which is illustrated above, are novel. They represent a further feature of the present invention and can be jointly defined by formula (VIII) below:

(VIII)

in which Alk is a $(C_1-C_4)$alkyl group, R* is hydrogen or a protecting group P*, as defined above, and R is hydrogen, a protecting group P', as defined above, or a heterocycle of structure (IX):

(IX)

in which Hal, X, Y and Z are as defined above, R* being other than hydrogen if R is hydrogen or a group of structure (IX).

The salts of the compounds of formula (VIII), where appropriate, also form part of the invention.

Among the compounds of formula (VIII) and their salts, 1-benzyl-4-acetylamino-4-methylpiperidine;
1-benzyl-4-t-butoxycarbonylamino-4-methylpiperidine;
4-amino-1-benzyl-4-methylpiperidine and its salts;
4-acetylamino-4-methylpiperidine and its salts;
4-t-butoxycarbonylamino-4-methylpiperidine and its salts;
4-acetylamino-1-(6-chloropyridin-2-yl)-4-methylpiperidine;
4-t-butoxycarbonylamino-1-(6-chloropyridin-2-yl)-4-methylpiperidine;
4-acetylamino-1-(4-chloropyrimidin-2-yl)-4-methylpiperidine;
4-t-butoxycarbonylamino-1-(4-chloropyrimidin-2-yl)-4-methylpiperidine;
4-acetylamino-1-(2-chloropyrimidin-4-yl)-4-methylpiperidine;
4-t-butoxycarbonylamino-1-(2-chloropyrimidin-4-yl)-4-methylpiperidine;
4-acetylamino-1-(6-chloropyrazin-2-yl)-4-methylpiperidine; and
4-t-butoxycarbonylamino-1-(6-chloropyrazin-2-yl)-4-methylpiperidine
are particularly preferred.

The compounds of formula (I) as defined above, and their pharmaceutically acceptable salts, have very valuable and unexpected pharmacological properties. In particular, these products possess a potent and selective agonistic activity towards the serotonin 5-$HT_3$ receptor.

The affinity of the compounds of formula (I) for the 5-$HT_3$ receptors was demonstrated with the aid of in vitro binding assays using the 5-$HT_3$ binding sites present in the rat cerebral cortex (G. J. Kilpatrick, B. J. Jones and M. B. Tyers, Identification and distribution of 5-$HT_3$ receptors in rat brain using radioligand binding. Nature, 1987, 330, 746–8) and, as the labeled ligand, [$^3$H] BRL 43694 (granisetron), which is a potent and specific 5-$HT_3$ receptor antagonist.

The preparation of the membranes and the binding test were carried out according to the method described by Nelson and Thomas (D. R. Nelson and D. R. Thomas, [$^3$H] BRL 43694 (granisetron), a specific ligand for 5-$HT_3$ binding sites in rat brain cortical membranes. Biochem. Pharmacol., 1989, 38, 1693–5).

The results were evaluated with non-linear fitting methods: "Accufit saturation" for the saturation studies (H. A. Feldman, Mathematical theory of complex ligand-binding systems at equilibrium: some methods of parameter fitting. Analyt. Biochem., 1972, 48, 317–38) and "Accufit competition" for the displacement studies (H. A. Feldman, D. Rodbard and D. Levine, Mathematical theory of cross reactive radioimmunoassay and ligand-binding systems at equilibria. Analyt. Biochem., 1972, 45, 530–56).

In these in vitro assays, the compounds of formula (I) are very potent in the displacement of [$^3$H] BRL 43694, used at a concentration of 0.5 nM. In particular, they are much more potent than serotonin and 2-methylserotonin and also more potent and/or more selective than the compounds not alkylated in the 4-position of the piperidine, described in patent application EP-A-506545.

Furthermore, the compounds of formula (I) are devoid of activity towards receptors other than the 5-$HT_3$ receptor, more particularly towards the serotoninergic, dopaminergic, adrenergic, histaminergic and muscarinic receptors, as is apparent from conventional binding tests.

The compounds of formula (I) also possess an intestinal prokinetic activity, associated with their action as 5-$HT_3$ agonists, in the rat fecal elimination test described in patent application EP-A-506545, in which, at low doses, they showed a good stimulating activity on fecal elimination.

The compounds of formula (I) have a low toxicity compatible with their use as drugs.

The compounds of formula (I) and their pharmaceutically acceptable salts can therefore be used for the preparation of drugs indicated in the treatment and/or prophylaxis of impairments and disorders of the peripheral and/or central serotoninergic system where the 5-$HT_3$ receptors are involved. This use and the associated method of treatment and/or prophylaxis constitute further features of the present invention.

These drugs can be used in the treatment and/or prophylaxis of dysthymic disorders, depression or psychotic disorders or in cases of anxiety. They can also be used in intestinal motility disorders, especially in the treatment of constipation or irritable bowel syndrome (IBS).

Thus, according to another of its features, the present invention relates to pharmaceutical compositions in which a compound of formula (I) or one of its pharmaceutically acceptable salts is present as the active principle, by itself or in association with any other pharmacologically compatible substance, and which are intended especially for oral and/or parenteral (sublingual, rectal, transdermal) administration.

The abovementioned pharmaceutical compositions are prepared by the customary methods well known in the field of galenics, the active principle of formula (I) or one of its pharmaceutically acceptable salts being mixed with the excipients usually employed, such as talc, gum arabic, lactose, starch, magnesium stearate, aqueous or non-aqueous vehicles, fats of animal or vegetable origin, paraffin derivatives, glycols, wetting agents, diapersants, emulsifiers, preservatives, flavorings, stabilizers, etc.

For oral administration, pharmaceutically appropriate forms include tablets, delayed-release tablets, coated tablets, gelatin capsules, suspensions, solutions, enteric forms and liposomal forms.

Aqueous or non-aqueous sterile injectable compositions can be prepared for parenteral administration, suppositories or microenemas for rectal administration, patches for transdermal administration and appropriate pharmaceutical forms for ocular or nasal administration.

The appropriate dosage of the active principle must be evaluated according to the mode of administration, the characteristics of the subject to be treated, such as age and body weight, and the severity of the complaints to be treated.

The dosage is generally between 0.05 and 100 mg per day, especially between 0.1 and 50 mg per day, and more appropriately between 0.5 and 20 mg per day, preferably between 1 and 10 mg per day.

This dosage can be subdivided into unit doses to be administered several times a day, preferably one to three times a day. Each unit dose contains from 0.05 to 100 mg, advantageously from 0.5 to 25 mg and preferably from 1 to 10 mg of active principle.

The Examples which follow illustrate the invention more clearly without however implying a limitation.

EXAMPLE 1

4-Amino-1-(6-chloropyridin-2-yl)-4-methylpiperdine hydrochloride a) 1-Benzyl-4-acetylamino-4-methylpiperdine—formula (VIII), Alk=methyl, R•=acetyl, R=benzyl 2.17 g (0.012 mol) of 1-benzyl-4-methyl-1,2,3,6-tetrahydropyridine are mixed with 0.9 g (0.022 mol) of acetonitrile, 3.6 ml of concentrated sulfuric acid are added cautiously and the mixture is heated at a temperature of 70° C. for 24 hours. While still hot, the mixture is poured into water/ice and a 20% solution of sodium carbonate is added until the pH is basic; the reaction medium is extracted with ethyl ether, dried over $Na_2O_4$ and evaporated to dryness under reduced pressure to give 1.17 g of the title compound (white solid, m.p. 103°–105° C.).

b) 4-Acetylamino-4-methylpiperidine—formula (VIII) Alk=methyl, R•=acetyl, R=H

A mixture of 0.7 g (0.00284 mol) of 1-benzyl-4-acetylamino-4-methylpiperidine, obtained according to step (a), and 0.07 g of 10% Pd/C in 10 ml of ethyl alcohol is hydrogenated at ambient pressure. After about 6 hours, the catalyst is filtered off and the filtrate is evaporated to dryness to give a white oil, which is treated with 2 ml of ethyl ether to isolate 0.4 g of the title combed (white solid, m.p. 75°–78° C.).

c) 4-Acetylamino-1-(6-chloropyridin-2-yl)-4-methylpiperidine—formula (VIII), Alk=methyl, R•=acetyl, R=structure (IX) where Hal=Cl, X=Y=Z=CH A mixture of 9 g (0.063 mol) of 2,6-dichloropyridine, 8 g (0.051 mol) of 4-acetylamino-4-methyl piperidine, obtained according to step (b), and 9.1 g (0.066 mol) of $K_2CO_3$ in 75 ml of n-pentanol is refluxed for 60 hours. It is evaporated to dryness and the residue is taken up with water (about 80 ml) and extracted with ethyl ether; the organic phase is dried over $Na_2SO_4$ and evaporated to dryness to give a solid which, when treated with hexane, gives 6.9 g of the compound indicated above (m.p. 77°–80° C.).

d) 4-amino-1-(6-chloropyridin-2-yl)-4-methylpiperidine hydrochloride

A mixture of 6.8 g (0.025 mol) of 4-acetylamino-1-(6-chloropyridin-2-yl)-4-methylpiperidine, obtained in step (c), and 80 ml of 6M hydrochloric acid is refluxed for 24 hours. The solution is concentrated by the addition of methanol to form an azeotrope and the residue is crystallized from absolute ethanol to give 2.5 g of the title compound (m.p.≈300° C.).

Elemental analysis: found: basic N=5.38; total Cl=27.2 calculated: basic N=5.38; total Cl=27.1

EXAMPLE 2

4-amino-1-(4-chloropyrimidin-2-yl)-4-methylpiperidine maleate a) 1-Benzyl-4-acetylamino-4-methylpiperidine—formula (VIII), Alk=methyl, R•=acetyl, R=benzyl The product is obtained as described in Example 1 step (a).

a') 4-amino-1-benzyl-4-methylpiperidine-formula (VIII), Alk=methyl, R•=H, R=benzyl A solution of 26.35 g (0.113 mol) of 1-benzyl-4-acetylamino-4-methylpiperidine, obtained according to step (a), in 200 ml of 6N hydrochloric acid is refluxed for 48 hours. It is allowed to cool and a 30% solution of NaOH is added until the pH is basic. The reaction medium is extracted with methylene chloride, dried over $Na_2SO_4$ and evaporated to dryness. The residue is purified by chromatography using $CH_2Cl_2/MeOH=9/1$ as the eluant to give 16 g of a yellow oil corresponding to the title compound (IR spectrum/film: 2920 $cm^{-1}$).

a") 1-Benzyl-4-t-butoxycarbonylamino-4-methylpiperidine—formula (VIII), Alk=methyl, R•=BOC, R=benzyl 15.5 g (0.081 mol) of 4-amino-1-benzyl-4-methylpiperidine, obtained according to step (a'), are dissolved in 110 ml of anhydrous chloroform under a nitrogen atmosphere and a solution of 16.7 g (0.076 mol) of di-tert-butyl dicarbonate in 27 ml of chloroform is added slowly. The mixture is stirred at room temperature overnight. The solvent is evaporated off to give 24.0 g (0.079 mol) of a yellow oil corresponding to the title compound (IR spectrum: 3246 $cm^{-1}$, 1690 $cm^{31\ 1}$).

b) 4-t-Butoxycarbonylamino-4-methylpiperidine—formula (VIII), Alk=methyl, R•=BOC, R=H A mixture of 24 g (0.079 mol) of 1-benzyl-4-t-butoxycarbonylamino-4-methylpiperidine, obtained according to step (a"), 1.5 g of 10% Pd/C and 250 ml of ethyl alcohol is hydrogenated at ambient pressure. After about 24 hours, the catalyst is filtered off and the solvent is evaporated off to dryness to give 16.5 g of the title compound (IR spectrum/KBr: 3246 $cm^{-1}$, 1690 $cm^{-1}$).

c) 4-t-Butoxycarbonylamino-1-(4-chloropyrimidin-2-yl)-4-methylpiperidine-formula (VIII), Alk=methyl, R•=BOC, R=structure (IX) where Hal=Cl, X=Y=CH, Z=N, and 4-t-butoxycarbonylamino-1-(2-chloropyrimidin-4-yl)-4-methylpiperidine—formula (VIII), Alk=methyl, R•=BOC, R=structure (IX) where Hal=Cl, Y=Z=CH, X=N A mixture of 3.13 g (0.0146 mol) of 4-t-butoxycarbonylamino-4-methylpiperidine, obtained according to step (b), 2.17 g (0.0146 mol) of 2,4-dichloropyrimidine, 1.48 g (0.0146 mol) of triethylamine and 100 ml of anhydrous toluene is refluxed for 24 hours. It is allowed to cool, the reaction by-products are filtered off and the solvent is evaporated off. The residue consists of a mixture of the two isomers indicated in the title and gives two spots in TLC. The two compounds are separated by chromatography on a column of silica gel using $CH_2Cl_2$/MeOH=98/2 as the eluent to give the following two products:

1.2 mg of 4-t-butoxycarbonylomino-1-(4-chloropyrimidin-2-yl)-4-methylpiperidine in the form of a pale yellow oil, corresponding to the first spot eluted (IR spectrum/KBr: 3245 $cm^{-1}$, 1675 $cm^{-1}$), and 3.3 g of 4-t-butoxycarbonylomino-1-(2-chloropyrimidin-4-yl)-4-methylpiperidine, m.p. 119°–120° C., in the form of a white solid, corresponding to the second spot eluted.

d) 4-Amino-1-(4-chloropyrimidin-2-yl)-4-methylpiperidine maleate

A solution of 2.22 g (0.0068 mol) of 4-t-butoxycarbonylamino-1-(4-chloropyrimidin-2-yl)-4-methylpiperidine (step c) in 25 ml of anhydrous methylene chloride is cooled under a nitrogen atmosphere and 5 ml of anisole and 25 ml of trifluoroacetic acid are added slowly. The mixture is stirred for 1 hour at room temperature and 25 ml of a 30% solution of NaOH are added slowly. The reaction medium is extracted with methylene chloride and dried over $Na_2SO_4$ and the solvent and the anisole are evaporated off under reduced pressure. The residue is purified by chromatography using $CH_2Cl_2$/MeOH=9/1 as the eluent to give 4-amino-1-(4-chloropyrimidin-2-yl)-4-methylpiperidine as the base, which is treated with maleic acid in an ethanol/isopropyl ether mixture. The maleate obtained in this way is isolated by filtration (m.p. 154°–155° C.).

Analysis for $C_{10}H_{15}ClN_4 \cdot C_4H_4O_4$: calculated: C 49.06—H 5.59—N16.34 found: C 47.68—H5.70—N15.70

EXAMPLE 3

4-Amino-1-(2-chloropyrimidin-4-yl)-4-methylpiperidine maleate

The procedure described in Example 2 is followed up to the end of step (c). A solution of 6.81 g (0.021 mol) of 4-t-butoxycarbonylamino-1-(2-chloropyrimidin-4-yl)-4-methylpiperidine (step c) in 80 ml of anhydrous methylene chloride is cooled under a nitrogen atmosphere and 16.4 ml of anisole and 83 ml of trifluoroacetic acid are added slowly. The mixture is stirred for 1 hour at room temperature and 80 ml of a 30% solution of NaOH are added slowly. The reaction medium is extracted with methylene chloride and dried over $Na_2SO_4$ and the solvent and the anisole are evaporated off under reduced pressure to give 4-amino-1-(2-chloropyrimidin-4-yl)-4-methylpiperidine as the base, which is treated with maleic acid in an ethanol/ethyl ether mixture. The maleate obtained in this way is isolated by filtration (yield 65%, m.p. 125°–126° C.).

Analysis for $C_{10}H_{15}ClN_4 \cdot C_4H_4O_4$: calculated: C 49.06—H 5.59—N 16.34 found: C 48.05—H 5.70—N 15.76

EXAMPLE 4

4-Acetylamino-1-(4-chloropyrimidin-2-yl)-4-methyl piperidine—formula (VIII), Alk=methyl, R•=acetyl, R=structure (IX) where Hal=Cl, X=Y=CH, Z=N, and 4-acetylamino-1-(2-chloropyrimidin-4-yl)-4-methyl piperidine—formula (VIII), Alk=methyl, R•=acetyl, R=structure (IX) where Hal=Cl, Y=Z=CH, X=N a) and b)

The procedure described in Example 3 steps (a) and (b) is followed.

c) A mixture of 0.8 g (0. 0051 mol) of 4-methyl-4-acetylamtnopiperidine, obtained according to step (b), 0.76 g (0.0051 mol) of 2,6-dichloropyrimidine and 0.51 g (0.0051 mol) of triethylamine in 10 ml of toluene is refluxed for 36 hours. It is allowed to cool, the by-products are filtered off and the solvent is evaporated off to dryness to give 0.9 g of a yellow oil, which consists of a mixture of the two isomers indicated in the title and gives two spots in TLC. The two compounds are separated by chromatography on a column of silica gel using $CH_2Cl_2$/MeOH=95/5 as the eluent to isolate the following two products:

120 mg of 4-acetylamino-1-(4-chloropyrimidin-2-yl)-4-methylpiperidine, m.p. 118°–120° C., corresponding to the first spot eluted, and 320 mg of 4-acetylamino-1-(2-chloropyrimidin-4-yl)-4-methylpiperidine, m.p. 173°–175° C., corresponding to the second spot eluted.

EXAMPLE 5

4-Amino-1-(6-chloropyrazin-2-yl)-4-methylpiperidine maleate a) and b)

The procedure described in Example 1 steps (a) and (b) is followed.

c) 4-Acetylamino-1-(6-chloropyrazin-2-yl)-4-methylpiperidine—formula (VIII), Alk=methyl, R•=acetyl, R=structure (IX) where Hal=Cl, X=Z =CH, Y=N A mixture of 1.0 g (0.0064 mol) of 4-acetylamino-4-methylpiperidine, 0.95 g (0.0064 mol) of 2,6-dichloropyrazine and 0.65 g (0.0064 mol) of triethylamine in 10 ml of toluene is refluxed for 24 hours. It is allowed to cool, the reaction by-products are filtered off and the solvent is evaporated off under reduced pressure. The residue is purified by chromatography using $CH_2Cl_2$/MeOH=98/2 as the eluent to give an oil, which solidifies on treatment with 10 ml of ethyl ether (m.p. 147°–148° C.).

d) 4-Amino-1-(6-chloropyrazin-2-yl)-4-methylpiperidine maleate 0.37 g (0.0013 mol) of 4-acetylamino-1-(6-chloropyrazin-2-yl)-4-methylpiperdine, obtained in step (c), in 10 ml of 6N hydrochloric acid is refluxed for 14 hours. The mixture is allowed to cool and a 30% solution of NaOH is added until the pH is alkaline. The reaction medium is extracted with methylene chloride, dried over $Na_2SO_4$ and evaporated to dryness. The residue is purified by chromatography using $CH_2Cl_2$/MeOH=7/3 as the eluent, to give 4-amino-1-(6-chloropyrazin-2-yl)-4-methylpiperidine in the form of an oil, which is treated with maleic acid in an ethanol/ethyl ether mixture. The corresponding maleate is isolated by filtration (m. p. 167°–168° C.).

Analysis for $C_{10}H_{15}ClN_4 \cdot C_4H_4O_4$: calculated: C 49.05—H 5.59—N 16.35 found: C 48.67—H 5.42—N 15.93

EXAMPLE 6

4-Amino-1-(6-bromopyridin-2-yl)-4-methylpiperidine hydrochloride

The procedure of Example 1 is followed using 2,6-dibromopyridine instead of 2,6-dichloropyridine in step (d). This gives 4-amino-1-(6-bromopyridin-2-yl)-4-methylpiperidine in the form of the hydrochloride.

What is claimed is:

1. A compound of formula (VIII):

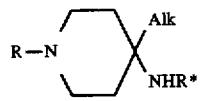
(VIII)

in which Alk is a $(C_1-C_2)$alkyl group, R* is hydrogen or a protecting group cleavable by hydrolysis and R is hydrogen, a protecting group cleavable by reduction or a heterocycle of structure (IX):

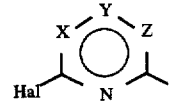
(IX)

in which Hal is a halogen atom and one of X, Y and Z is a nitrogen atom and the others are —CH=, and its salts, R* being other than hydrogen if R is hydrogen or a group of structure (IX).

2. A compound of formula (VIII):

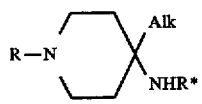
(VIII)

in which Alk is a $(C_1-C_4)$alkyl group, R* is hydrogen or a protecting group cleavable by hydrolysis and R is hydrogen, a protecting group cleavable by reduction or a heterocycle of structure (IX):

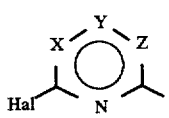
(IX)

in which Hal is a halogen atom and X, Y and Z are each —CH=, and its salts, R* being other than hydrogen if R is hydrogen or a group of structure (IX).

* * * * *